United States Patent [19]

Crea et al.

[11] Patent Number: 5,700,677
[45] Date of Patent: Dec. 23, 1997

[54] PROTEIN ANALOGUES OF TISSUE PLASMINOGEN ACTIVATOR

[75] Inventors: Roberto Crea, Bulingame, Calif.; Roy Hoi Loi Pang, Medway, Mass.; Hermann Oppermann, San Francisco, Calif.; Peter C. Keck, Millbury, Mass.; Gabriel Alvarado-Urbina, Nepean, Canada; Gay-May Wu, Westboro; Charles M. Cohen, Medway, both of Mass.

[73] Assignees: Creative BioMolecules, Inc., Hopkinton, Mass.; A. Menarini S.A.S., Firenzi, Italy

[21] Appl. No.: 799,769

[22] Filed: Nov. 27, 1991

Related U.S. Application Data

[63] Continuation of Ser. No. 562,454, Aug. 2, 1990, abandoned, which is a continuation of Ser. No. 845,541, Mar. 28, 1986, abandoned.

[51] Int. Cl.[6] .................... C12N 15/00; C07K 14/745; A61K 38/49
[52] U.S. Cl. .................... 435/226; 435/212; 435/219; 435/69.7; 530/300; 530/324; 530/350
[58] Field of Search .................... 530/300, 324, 530/350, 387; 435/212, 219, 226, 69.7

[56] References Cited

U.S. PATENT DOCUMENTS

| | | | |
|---|---|---|---|
| 4,518,520 | 5/1985 | Olson | 435/68 X |
| 4,558,010 | 12/1985 | Hung et al. | 435/212 |
| 4,970,159 | 11/1990 | Dodd | 435/226 |

FOREIGN PATENT DOCUMENTS

| | | |
|---|---|---|
| 0093619 | 4/1983 | European Pat. Off. . |
| 352119 | 1/1990 | European Pat. Off. . |
| 2119804 | 11/1983 | United Kingdom . |
| 8400774 | 3/1984 | WIPO .................... 435/172.3 |

OTHER PUBLICATIONS

Hollander, W. et al, *Artherosclerosis*, vol. 34, p391–405, 1979.
Colbert, D. et al, *J. Biolog. Response Modifiers*, vol. 3, p255–259, 1984.
Nilsson, B., et al, *The EMBO Journal*, vol. 4, No. 4, pp. 1075–1080, Apr., 1985.
van Zonneveld, A–J et al., *PNAS USA* 83:4670–4674; 1986.
Ny, T. et al., *PNAS USA* 81: 5355–5359. 1984.
Kagitani, H. et al., *FEBS* 189(1):145 (1985).
Bode, C. et al., *Science* 229:765–767 (1985).
Sevilla, C.L. et al., *Fed. Proc. Fed. Am. Soc. Exp. Biol.* 44:1073 (1985).
Ito, R.K. et al., *Fed. Proc. Fed. Am. Soc. Exp. Biol.* 44:1846 (1985).

*Primary Examiner*—Marianne P. Allen
*Attorney, Agent, or Firm*—Testa, Hurwitz & Thiebault, LLP

[57] ABSTRACT

Protein analogues of tissue plasminogen activator (tPA) are described. The analogues exhibit the proteolytic function of natural tPA and optionally fibrin binding activity, but are molecules, generally of lower molecular weight than natural tPA, designed for efficient expression in prokaryotic host cell systems. The analogues can comprise a catalytic fragment of tPA or a catalytic fragment of tPA linked to a polypeptide which stabilizes the catalytic fragment, provides for efficient expression of the fragment or confers a fibrin binding capability. Fibrin binding polypeptides can be a polypeptide fragments derived from tPA which embody the fibrin binding domain(s) of natural tPA or they can be an exogenous (non-tPA) polypeptides of eukaryotic or prokaryotic origin which exhibit fibrin binding affinity such as the antigen binding fragment of an antifibrin immunoglobulin or the B domain of protein A. Genetic constructs for expression of the analogues are also provided.

12 Claims, 10 Drawing Sheets

```
         10         20         30         40         50         60         70         80         90        100
GAATTCATGTCTTACCAGGTTATCTGCCGTGACGAAAAACTCAGATGATCACCAGCACCAGTCTTGGCTGCCGTCCGGTTCTGCGTTCTAACCGTG
GluPheMetSerTyrGlnValIleCysArgAspGluLysThrGlnMetIleTyrGlnGlnHisGlnSerTrpLeuArgProValLeuArgSerAsnArgV
EcoRI 110        120        130        140        150        160        170        180        190        200
TTGAATACTGCTGGTGCAACTCCGGCCGTTGCCACTCTGTTCCGGTTAAATCCTGTTCCAGGAACCGCGTTGCTTCAACGGTGCTGTACCTGCCAGCA
alGluTyrCysTrpCysAsnSerGlyArgAlaGlnCysHisSerValProValLysSerCysSerGluProArgCysPheAsnGlyThrCysGlnGly
                           EagI                            PstI                                    KpnI
                           XmaIII 210        220        230        240        250        260        270        280        290        300
GGCTCTGTACTTCTCTGACTTCGTTTGCCAGTGCCCGGAAGTTTCTGCTACGAAGACCAGGGT
nAlaLeuTyrPheSerAspPheValCysGlnCysProGluValCysGlyPheAlaGlyLysCysCysGluIleAspThrArgAlaThrCysTyrGluSerGlnGly
                                                             ClaI                               BbvII 310        320        330        340        350        360        370        380        390        400
ATCTCTTACCGCGGCCACTGGGTCCACGGCTGAGTCTGGCGCCGAATGCTGGAACTCTCTGGCTCAGAAACCGTACTCTGGTCGTCGTC
IleSerTyrArgGlyHisTrpSerThrAlaGluSerGlyAlaGluCysTrpAsnSerLeuAlaGlnLysProTyrSerGlyArgArgP
SacII NarI BsaI Bs 410        420        430        440        450        460        470        480        490        500
CGGACGCTATCCGTCTGGGTAACCACTGCCGTAACCATGGTGCTACGTTTTTAAAGCTGGTAAATACTC
roAspAlaIleArgLeuGlyLeuGlyAsnHisAsnTyrCysArgAsnProAspSerLysProTrpCysTyrValPheLysAlaGlyLysTyrSe
pmII                                BstEII                           RsrII                  NcoI      DraI 510        520        530        540        550        560        570        580        590        600
TTCTGAATTTTGCTCTACCCCGGCATGCTCTGAAGGTAACTCTGACTGCTTCGGTTACCGTGGTACCACCACTCTGACCGAATCT
rSerGluPheCysSerThrProAlaCysSerGluGlyAsnSerAspCysPheGlyTyrArgGlyThrThrThrLeuThrGluSer
                        SphI                                                  KpnI
```

Fig. 2A

```
         610       620       630       640       650       660       670       680       690       700
GGCGCCTCCTGCCTGCCATGGAACCTGATCGGCAAAGTTACACTGTTCATCGGTGCTCAGGCACTGGGCCTGGGCAAACACAACT
GlyAlaSerCysLeuProTrpAsnSerMetIleLeuIleGlyLysValTyrThrAlaGlnAsnProSerAlaGlnAlaLeuGlyLeuGlyLysHisAsnT
  NarI            NcoI
         710       720       730       740       750       760       770       780       790       800
ACTGCCGTAACCCGGACGGTGACGCTAAGCCGTGTCGTCCACGTTCTGAAGAAACCGTCGTCTGACTGGGAGTACTGCGACGTCCCGTCCTGCAGCACCTG
yrCysArgAsnProAspGlyAspAlaLysProTrpCysHisValLeuLysAsnArgArgLeuThrTrpGluTyrCysAspValProSerCysSerThrCy
                   EspI                                                    ScaI     AatII     PstI
         810       820       830       840       850       860       870       880       890       900
CGGCCCTGCGTCAGTACTCTCAGCCGCAGTTCCGTATCAAAGGCGGTCTGTTCGCTGATATCGCTTCCACCCGTGGCAGGCTGCAATCTTCGCTAAACAC
sGlyLeuArgGlnTyrSerGlnProGlnPheArgIleLysGlyGlyLeuPheAlaAspIleAlaSerHisProTrpGlnAlaAlaIlePheAlaLysHis
  ScaI                                                                          EcoRV
         910       920       930       940       950       960       970       980       990      1000
CGTCGGTCTCCGGGTGAACGGTTCCTGTGCGGTGGCATCCTGATCAGCTCCTGGATTCTGCTGCACACTGCTTCCAGGAACGTTTCCGCCGC
ArgArgSerProGlyGluArgPheLeuCysGlyGlyIleLeuIleSerSerCysTrpIleLeuSerAlaAlaHisCysPheGlnGluArgPheProProH
                                             BclI
        1010      1020      1030      1040      1050      1060      1070      1080      1090      1100
ACCACCTGACTGTTATCCTCGGCCGTGTTGTACCGTGTGCTGCGGGAAGAGGAAGAAATTGAAGTTGAAAAATACATCGTTCACAAAGAGTTCGA
isHisLeuThrValIleLeuGlyArgValValProValValArgThrTyrArgValValProGlyValProGlyLysPheGluValGluLysTyrIleValHisLysGluPheAs
    EagI                        SeaI                                                  AsuII
    XcaIII
        1110      1120      1130      1140      1150      1160      1170      1180      1190      1200
CGATGACACTTACGACAACGATATCGCTCTGCTGAAACTGCTGCAGTCGAAATCTGACTCTTCCGTTGCGCTCAGGAGAGCTCCGTTGTACGCACTGTTGCCTGCCG
pAspAspThrTyrAspAsnAspIleAlaLeuLeuGlnLeuLeuLysSerAspSerSerArgCysAlaGlnGluSerSerArgCysAlaValArgThrValCysLeuPro
    EcoRV       PstI                                                        SacI
                PvuII
```

Fig. 2B

```
         1210      1220      1230      1240      1250      1260      1270      1280      1290      1300
     CCGGCCGACCTCCAGCTGCCGACTGGACTGAATGCGAGCTGTCCGGCTACGGCAAGCAGCTTTGTCTCCCGTTCTACTCTGAACGTCTGAAGGAAG
     ProAlaAspLeuGlnLeuProAspTrpThrGluCysGluLeuSerGlyTyrGlyLysLysHisGluAlaLeuSerProPheTyrSerGluArgLeuLysGluA
     aeI       PvuII    BsaI                                         HindIII
     EagI
     XmaIII
         1310      1320      1330      1340      1350      1360      1370      1380      1390      1400
     CTCACGTTCGTCTGTACCCGTCCTCCCCCGTTGCACTTCCCAGCACCTGACTGTAACCTGCTGACTGTGCGCTGGTGGACACTCGTTCTGG
     laHisValArgLeuTyrProSerSerArgCysThrSerArgGlnHisLeuLeuAsnLeuThrValThrAspAsnMetLeuCysAlaGlyAspThrArgSerGl
         1410      1420      1430      1440      1450      1460      1470      1480      1490      1500
     CGGTCCGCAGGCAAACCTGCACGACGCATGCCAGGGCGACTCTGGTGGCCCGCTGTTGCCTGAACGACGTCGCATGACTCTGGTTGGCATCATCTCT
     yGlyProGlnAlaAsnLeuHisAspAlaCysGlnGlyAspSerGlyGlyProLeuValCysLeuAsnAspValArgMetThrLeuValGlyIleIleSer
     RsrII SphI
      1510 1520 1530 1540 1550 15b0 1570 1580 1590 1600
     TGGGGCCTGGGCTGCGGTCAGAAAGACGTCCCGGGCGTGTACACTAAGGTTACCAACTACCTGATTCGTGACAACATGCGTCCGTAGGATCC
     TrpGlyLeuGlyCysGlyGlnLysAspValProGlyValTyrThrLysValThrAsnTyrLeuAspTrpIleArgAspAsnMetArgPro#am
                   AatIISmaI                          BstXI                                BamHI
                   XmaI                       BstEII
```

Fig. 2C

```
         10         20         30         40         50         60         70         80         90        100
GAATTCATGGCTGACAACAAATTCAACAAGGAACAGCAGAACGCGTTCTACGAGATCTTGCACCTGCCGAACCTGAACGAGCAGCGTAACGGCTTCA
GluPheMetAlaAspAsnLysPheAsnLysGluGlnGlnAsnAlaPheTyrGluIleLeuHisLeuProAsnLeuAsnGluGlnArgAsnGlyPheI
EcoRI                                              MluI       BglII
                                                   XanI 110        120        130        140        150        160        170        180        190        200
TCCAAGCTTGAAAGACGACCCGTCTGAGAGCTAACCTGCTGGCAGAGGCCAAGAAACTGAACGACGCTCAGGCGCCGAAGAGTACTTGCGGTCTACG
leGlnSerLeuLysAspAspProSerGlnSerAsnLeuLeuAlaAsnLeuAlaAlaLysLysLeuAsnAspAlaGlnAlaProLysSerThrCysGlyLeuAr
    HindIII                                                                              NarI     ScaI 210        220        230        240        250        260        270        280        290        300
TCAATACTCTCAGCCGCAGTTCCGTATCAAAGGCGGTCTGTTCGGTATATCGCTGCTGATATGCTTCCCACCCGTGGCAGGCTGCAATCTTCGCTAAACCGTCGTCT
gGlnTyrSerGlnProGlnPheArgIleLysGlyGlyLeuPheAlaAspIleAlaSerHisProTrpGlnAlaAlaIlePheAlaAlaLysHisArgArgSer
                                            EcoRV 310        320        330        340        350        360        370        380        390        400
CCGGGTGAACGGTTCCTGTGCCGCTGGCATCCTGATCAGCTCCTGCTGGATTCTGTCGCTCTGCTTCCGAAGAACGTTCCGCCGCACCACCTGA
ProGlyGluAsnGlyPheLeuCysArgTrpHisProAspGlnLeuLeuLeuLeuAspSerValAlaLeuLeuPheArgArgThrPheArgArgThrThr
                              BclI 410        420        430        440        450        460        470        480        490        500
CTGTTATCCTCGGCCTACTTACCGTGTTGTACCGGGGAAGAAGAGAAATTCGAAGTTGAAAAATACATCGTTGAAGAGTTCGACGATGACAC
hrValIleLeuGlyArgThrTyrArgValValProGlyGluGluGluGluGlnLysPheGluValGluLysTyrIleValHisLysGluPheAspAspTh
EagI         SmaI                                           AsuII
XmaIII       XmaI
```

Fig.5A

```
        510       520       530       540       550       560       570       580       590       600
TTACGACAACGATATCGCTCTGCTGCAGCTGAAATCTGACTCTTCCCGTTGCCTCAGGAGAGCTCCGTTGACGCACTGTTTGCCTGCCGCGGCCGAC
rTyrAspAsnAspIleAlaLeuLeuGlnLeuLysSerAspSerSerArgCysAlaGlnGluSerValValArgThrValCysLeuProAlaAsp
        EcoRV                   PstI                          SacI                       EagI
                                  PvuII                                                  NaeI
                                                                                         XmaIII 610       620       630       640       650       660       670       680       690       700
CTCCAGCTGCCGGACTGAATGCAGCTGTCCGGCTACGGCAAGCTTGTCTCCTACTCTGAACGTCTGAAGGAAGCTCACGTTC
LeuGlnLeuProAspTrpThrThrGluCysGluSerGlyLeuGluSerGlyLeuTyrGlyLysHisGluAlaLeuSerProPheTyrSerGluArgLeuLysGluAlaHisValA
            PvuII         BsmI                           HindIII 710       720       730       740       750       760       770       780       790       800
GTCTGTACCCGTCCTCCCCGTTGCACTTCCCAGCACCTGCTGAACCTGACTGTAACCGACAACATGCTGTGCGCTGGTGACACTCGTTCTGGCGGTCCGCA
rgLeuTyrProSerSerArgCysThrSerGlnHisLeuLeuAsnLeuThrValThrAspAsnMetLeuCysAlaGlyAspThrArgSerGlyGlyProGl
                                                                                              RsrII 810       820       830       840       850       860       870       880       890       900
GGCAAACCTGCACGACGCATGCCAGGCGACTCTGGTGGCCCTGGTTGCCTGAACGACGGTCGATGACTCTGGTTGGCATCATCTCTTGGGCCTG
nAlaAsnLeuHisAspAlaCysGlnGlyAspSerGlyGLyProLeuValCysLeuAsnAspGlyArgMetThrLeuValGlyIleIleSerTrpGlyLeu
              SphI                              AatIISmaI                              BstXI
                                                 XmaI                                   BstEII 910       920       930       940       950       960       970       980       990       1000
GGCTGCGGTCAGAAAGACGTCCCGGGCGTGTACACTAAGGTTACCAACTACCTGGACTGGATTCGTGACAACATGCGTCCGTAGGATCC
GlyCysGlyGlnLysAspValProGlyValTyrThrLysValThrAsnTyrLeuAspTrpIleArgAspAsnMetArgPro#amAsp
                                                                                    BamHI
```

Fig.5B

PROTEIN ANALOGUES OF TISSUE PLASMINOGEN ACTIVATOR

STATEMENT OF RELATED CASES

This application is a continuation of U.S. application Ser. No. 07/562,454, filed Aug. 2, 1990, now abandoned, which was a continuation of U.S. application Ser. No. 06/845,541, filed Mar. 28, 1986, now abandoned.

TECHNICAL FIELD

This invention is in the fields of genetic and protein engineering.

BACKGROUND

Tissue plasminogen activator (tPA) is a key enzyme in a naturally occurring system by which mammals dissolve blood clots. Its value as a therapeutic agent, especially in the emergency treatment of coronary arterial or other vascular occlusions is widely recognized. tPA is a serine protease which catalyzes the conversion of the inactive protein plasminogen into plasmin, the active form. Plasmin then dissolves the fibrin clot. tPA can bind specifically to fibrin molecules thus limiting its proteolytic action to the location of the clot. Other plasminogen activators presently available, urokinase, which is also derived from mammalian sources, and streptokinase, which is derived from bacteria, do not exhibit this fibrin binding specificity. (Prourokinase however can bind to fibrin specifically)

Human tPA has been prepared in highly purified form from human melanoma cells by Rijken and Collen, *J. Biochem.* (1981) 256:7035–7041. Melanoma tPA (mtPA) is an approximately 68 kd protein which is highly glycosylated. Glycosylation is not believed to be essential to activity because enzymatic deglycosylation by endoglycosidase F does not reduce the activity of the protein, and tPA prepared from melanoma cells grown in the presence of the glycosylation inhibitor tunicamycin retains activity.

The complete amino acid sequence of tPA has been deduced from the cDNA sequence. See Pennica, D. et al, *Nature* (1983) 301:214–221. Recombinant forms of rtPA have been produced in bacteria and in mammalian cells using appropriate control DNA sequences ligated to tPA cDNA (made from melanoma cell mRNA). The resulting protein product has the same amino acid sequence as the secreted protein from the melanoma cells.

Naturally occurring human tPA has the amino acid sequence and putative secondary structure shown in FIG. 1. The figure also shows the signal sequences which are absent in the mature tPA protein. The sequence of the mature protein is considered to begin at position 1 designated in the figure and contains 527 amino acids.

The mature protein is thought to be composed of three major domains. The N-terminal 1–80 (approx) amino acids are designated the finger region. The sequence between approximately amino acid 80 and amino acid 270 is held in a double kringle conformation by six disulfide bonds. The kringle region is putatively involved in the fibrin binding properties of tPA. The portion of the molecule responsible for the enzymatic action of tPA—the catalytic domain—is the region of amino acids 270–527 approximately. This portion of the molecule appears to have the characteristics of a serine protease.

Extensive studies have shown that various regions of tPA are homologous to regions of other proteins with related biological activities. For example, kringle structures have also been found in prothrombin, plasminogen and urokinase. The catalytic domain has some homology to the bovine serine proteases trypsin, chymotrypsin, and plasmin.

The tPA precursor zymogen is cleaved in vivo between the arginine at position 275 and the isoleucine residue at 276. Cleavage results in conversion of the zymogen to the active form of tPA.

Although the general parameters of production of recombinant proteins from bacterial hosts are understood, a number of practical problems are often encountered. When mammalian proteins are produced in prokaryotic host cells, often times either they are unstable or they are precipitated within the cell as "refractile" or "inclusion" bodies. In some instances, these insoluble proteins are improperly "folded", i.e. they are not processed by the host cell into the appropriate three dimensional structure that is optimal or even adequate for activity. Extensive efforts have been made to devise procedures to refold and to "reactivate" such proteins. See, for example, EPO publication 144,506, 1 August 1984, Genentech: U.S. Pat. No. 4,511,502, Builder and Ogez. The tPA protein is especially susceptible to improper folding because it contains 35 cysteine amino acid residues which are capable of forming disulfide bonds so as to stabilize whatever three dimensional structure, correct or incorrect, is generated in the expression system. Production of foreign proteins in mammalian cells generally results in forms of the proteins which more accurately reflect their native donformations, but mammalian cell production is expensive and more difficult to control.

DISCLOSURE OF THE INVENTION

This invention pertains to protein analogues of tissue plasminogen activator (tPA) which exhibit the proteolytic action of natural tPA and optionally exhibit fibrin binding properties but are molecules of lower molecular weight than natural tPA and are designed for high efficiency expression in prokaryotic expression systems. The tPA analogues* of this invention are proteins of lower molecular weight than natural human tPA. The analogues can a) consist of substantially only a catalytic fragment of tPA; or b) consist of a catalytic fragment of tPA linked to a polypeptide which provides a desirable property or function in addition to the catalytic function, provided that the polypeptide in combination with the catalytic fragment forms a molecule which can be refolded efficiently. In general, the fragment is of lower molecular weight than tPA.

* As used herein the term "tPA analogue" means a molecule other than tPA itself which comprises a catalytic fragment of tPA and which may include either an endogenous (tPA derived) or exogeneous (non-tPA) polypeptide which may have fibrin binding activity. The polypeptide, for example, can provide for i) stabilization of the catalytic fragment; or ii) fibrin binding activity.

Thus, in one embodiment, the tPA analogues of this invention comprise a catalytic fragment of tPA which contains the active enzyme sites for proteolysis. Analogues of this type have only the proteolytic properties of tPA. The preferred catalytic fragment is a fragment of tPA encompassing amino acids 262–527.

In preferred embodiments, the analogues comprise a functional catalytic fragment and a fibrin binding fragment which confers affinity for fibrin. The catalytic fragment is derived from the tPA molecule. The fibrin binding fragment can be derived either from fibrin binding domains of the tPA molecule or from exogenous polypeptides which have fibrin binding properties. For instance, the fibrin binding fragment may be an endogenous portion of the tPA molecule involved in fibrin binding (e.g., parts of the finger/kringle region). Portions of tPA responsible for instability or sub-optimal refolding of tPA expressed in prokaryotic host cells can be excluded from the analogue. Alternatively, the fibrin binding fragment of the analogues can be non-tPA fibrin binding polypeptides, i.e., exogenous polypeptide or protein fragments which confer fibrin binding affinity. Examples of exogenous fibrin binding polypeptides could include the antigen binding domain (Fab) of an antifibrin immunoglobulin (Ig), the B domain of protein A or other domains of protein A.

The tPA analogues are produced by recombinant DNA techniques. Although the analogues can be expressed in eukaryotic host cell systems, they are designed for the more economical and convenient expression in prokaryotic host cell systems, e.g., E. coli. Employing recombinant DNA techniques, the polydeoxynucleotides encoding the analogue are constructed and operably linked to control sequences of a suitable DNA expression vector. The recombinant vector is then used to transform the host cell. The transformed host cell is then cultured to produce the analogue which is then isolated from the host cell.

BRIEF DESCRIPTION OF THE DRAWINGS

FIG. 2 (A,B and C) shows the complete DNA sequence of a preferred embodiment of the synthetic tPA gene.

FIG. 5 (A and B) shows the nucleotide sequence of a DNA construct encoding a tPA analogue comprising the B domain of Protein A linked to a catalytic fragment of tPA and the amino acid sequence of the analogue.

BEST MODE OF CARRYING OUT THE INVENTION

Figure 1:
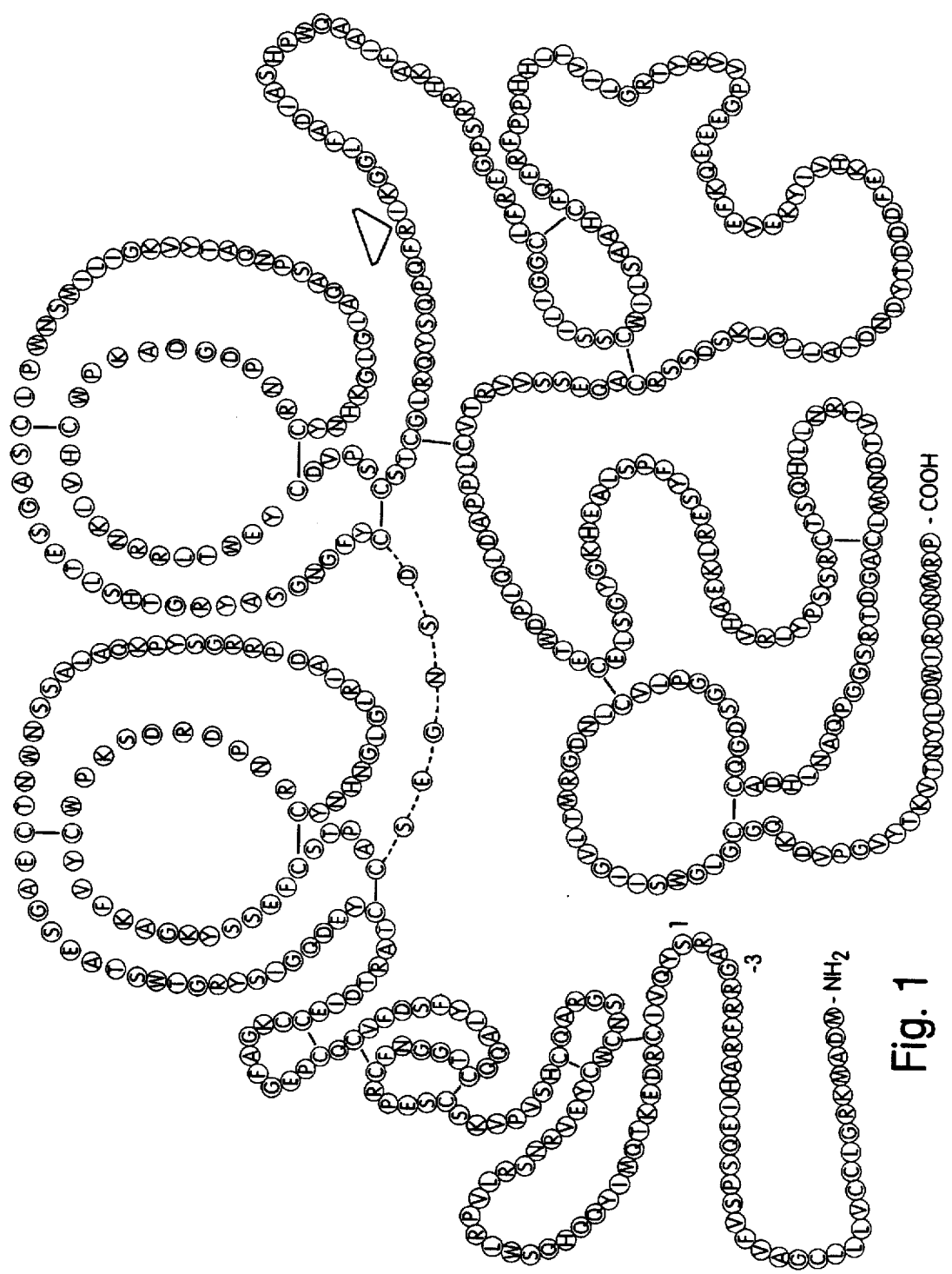
FIG. 1 is a schematic, two dimensional representation of the primary and secondary structure of tPA including the 37 amino acid signal peptide.

The tPA analogues of this invention comprise "recombinant" protein molecules which have the fibrinolytic activity of tPA and optionally the capability to bind to fibrin. The molecules are designed for highly efficient production in prokaryotic, especially E. coli. In preferred embodiments, the molecules are of lower molecular weight than natural tPA in order to provide for more efficient refolding and reactivation upon isolation from prokaryotic cells.

In one embodiment, the analogues comprise essentially only a catalytic fragment of the tPA molecule (designated $CF_{tPA}$). The preferred catalytic fragment is the portion of natural tPA encompassing amino acids 262–527 inclusive, i.e., the portion of the tPA molecule ranging from the serine/threonine residues 262 and 263 (which link the catalytic fragment to the second kringle of tPA) to the C-terminal proline residue. This preferred catalytic fragment can potentially form seven intramolecular disulfide bonds which can aid in proper conformational folding of the catalytic fragment and stabilization of its structure (See FIG. 1).

In another embodiment, the tPA analogues comprise $CF_{tPA}$ linked to a polypeptide which helps stabilize the catalytic fragment.

In the preferred embodiment, the tPA analogues have a fibrin binding capability. They comprise a catalytic fragment of tPA linked (either directly or through an intermediate polypeptide linker) to polypeptide which confers fibrin binding specificity. The polypeptide which provides fibrin binding specificity can be derived from "natural" tPA sequences involved in fibrin binding or exogenous amino acid sequences such as the B domain of protein A or the antigen binding fragment (Fab) of an antifibrin antibody.

In general, the tPA analogues of this invention can be represented by the formula:

$$H_2N-X-X-L-CF_{tPA}-COOH$$

In this depiction, $CF_{tPA}$ represents a catalytic fragment of tPA. The preferred catalytic fragment, as specified above, is the fragment encompassing amino acids 262–527 of natural tPA. L taken together with X represents a bond, or L individually represents a peptide bond linking a polypeptide X to $CF_{tPA}$ or L represents an oligopeptide linker of desired structure and function. It can be an amino acid sequence which provides a preferential site for cleavage. For example, L can be the cleavage site for Factor $X_a$. Incorporation of this site into the analogues provides for cleavage of X and $CF_{tPA}$ at the site.

The designation X represents a polypeptide, generally smaller in size than the complete finger/kringle region of tPA, linked (as a continuous polypeptide chain) to the catalytic fragment $CF_{tPA}$ either directly or via an oligopeptide linker L. (In preferred embodiments, when L is present, the combined size of X and L is of lower molecular weight than the complete finger/kringle region of tPA). X can be a "leader sequence" which provides for a more stable and/or more efficiently expressed tPA analogue. Preferably, the polypeptide X is a fibrin binding polypeptide. In this case, X may be selected from natural tPA fragments involved in fibrin binding. The selected fragments would have lower molecular weight than the combined finger/kringle region of tPA and accordingly the complete analog would be of lower molecular weight than tPA. The fibrin binding domain can be designed to exclude portions of the native molecule unnecessary for fibrin binding and/or portions which contribute to the instability or improper refolding of tPA.

X may be also selected from exogenous polypeptides sequences (those not found in tPA) of prokaryotic and/or eukaryotic origin which provide fibrin binding activity. An example of an exogenous eukaryotic protein fragment is the antigen binding domain of an immunoglobulin molecule which specifically bind fibrin. In analogues of this type, the variable region of an immunoglobulin light ($V_L$) or heavy chain ($V_H$) can be linked either directly or through a portion of the constant region of either chain to a catalytic fragment of tPA. This construct can be depicted as follows:

$$NH_2-V_{(H\ or\ L)}-[C_{(H\ or\ L)}]-CF_{tPA}-COOH$$

wherein V is the variable region of a heavy ($V_H$) or a light ($V_L$) chain of a fibrin specific antibody and C represents a portion of the constant region of the antibody which is optional, as indicated by the brackets.

Exogenous polypeptides may be chosen also from prokaryotic protein sequences which bind fibrin. A preferred prokaryotic polypeptide is the B domain of protein A which, surprisingly, has been found to provide fibrin binding specificity when joined to a catalytic fragment of tPA. Other domains of protein A, such as the E, B C, or D domains, may also provide fibrin binding capability. These protein domains may be present in single or multiple units.

Analogues containing the B domain of protein A can be represented by the formula:

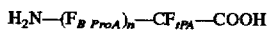

As above $CF_{tPA}$ signifies a catalytic fragment of tPA, preferably the tPA catalytic fragment spanning amino acid residues 262–527 inclusive. $F_{B\ ProA}$ designates the B domain of protein A or substantial equivalent thereof. Modified forms of the B domain can be used to enhance the specificity of fibrin binding and to reduce undesired immunogenicity of the segment. Multiple, sequentially aligned $F_{B\ ProA}$ units may be attached to $CF_{tPA}$ as indicated by the subscript n. Preferably, the number of $F_{B\ ProA}$ units may range from 1 to 5, most preferably, n is 1 or 2.

Analogues comprising the B domain of protein A linked to a catalytic fragment of tPA exhibit fibrinolytic activity which is plasminogen dependent and which can be completely neutralized by antibody against tPA. These analogues bind fibrin directly. Further, $(F_{B\ ProA})_n—CF_{tPA}$ analogues are less hydrophobic than natural tPA and, thus, may be suitable for intramuscular routes of administration.

The tPA analogues of this invention are designed to be produced by recombinant DNA techniques. The analogues can be expressed in prokaryotic host cell systems by standard techniques. Polydeoxynucleotides encoding the desired analogues can be constructed by conventional techniques of gene synthesis and gene splicing as set forth in more detail below.

Double stranded DNA constructs encoding the tPA analogues can be represented, in 5' to 3' orientation, as follows:

5' [DNA encoding X]- DNA encoding $CF_{tPA}$ 3'

The brackets indicate that DNA encoding X is optional. Thus, the contruct contains optionally a first DNA sequence encoding X and a second DNA sequence encoding $CF_{tPA}$. Where desired, a oligodeoxynucleotide encoding a linker oligopeptide L is interposed between the DNA sequence encoding X and the DNA sequence encoding $CF_{tPA}$. Nucleotides may be added to the 5' and 3' terminals of these constructs to provide restriction enzyme recognition sites for convenient insertion of the construct into DNA vectors.

When X is an exogenous, non-tPA polypeptide, DNA sequences encoding this portion of the analogue can be obtained from clonal cell lines harboring the DNA sequence. The cell lines can be obtained from commercial sources and the DNA sequence can be obtained by standard techniques of gene cloning. When the DNA sequences encoding the desired polypeptide X are known (as is the case for the B domain of protein A) or can be determined (sequenced), the polydeoxynucleotide can be synthesized by standard procedures such as the phosphotriester and phosphite triester techniques. DNA encoding the tPA derived fragments, e.g., $CF_{tPA}$, can be obtained from DNA sequences encoding tPA. As an example of a complete DNA construct, FIG. 5 shows the entire deoxynucleotide sequence of a gene construct encoding the analogue: $F_{B\ ProA}$ - $CF_{tPA}$. The amino acid sequence of the analogue is also given.

In the preferred embodiments, DNA sequences encoding the tPA-derived portions of the analogues are obtained from a synthetic tPA gene. For this purpose, applicants have synthesized a conveniently manipulable, synthetic tPA gene which encodes human tPA. The synthetic gene has been designed to be compatible with the *E. coli* codon bias for efficient expression. The synthetic DNA fragment encodes a protein having tPA activity and contains inherent characteristics which permit facile manipulation of subgenic DNA fragments. The preferred gene encodes a protein with an N-terminal serine (after the methionine corresponding to the start codon) although a useful variant is a fragment which contains three additional N-terminal amino acids, Gly-Ala-Arg, which precede the N-terminal serine exhibited by most native mature tPA, and which are sometimes retained by the mature sequence in the extracted protein.

The gene is bounded by additional short segments of DNA if necessary to provide start and stop codons for translation and to provide convenient restriction sites. Thus, the gene will contain approximately 3×527, or 1581 base pairs, with a few additional base pairs at each terminus.

The preferred tPA gene construct is shown in FIG. 2. It is prepared as set forth below in Example 1. The synthetic gene bears an additional 9 base pairs including the ATG start codon at the upstream end, and an additional 2 base pairs to complete the stop codon at the downstream terminus. By appropriate codon selection, the fragment is bounded by EcoRI and Bam H1 restriction sites. Additional restriction sites were designed into the molecule as shown in FIG. 2.

The particular sequence illustrated in FIG. 2 was designed using the criteria of compatibility with *E. coli* codon preference, the proper distribution of restriction enzyme sites across the gene, and the uniqueness of these sites within particular segments representing the whole. It is clear that alternate DNA fragments which encode substantially the entire tPA protein with different restriction sites could be constructed using different codon selection. The preferred design, however, permits easy segregation of the DNA into three "cassettes", each cassette corresponding to approximately a third of the molecule. By using this cassette-based construction, the resulting protein can be readily manipulated at the genetic level to represent an assembly of the most desirable portions in an optimal order.

In addition, during construction, restriction sites unique to individual cassette are included, thus permitting clean excision of shorter portions of the molecule. The sub-cassette fragments can be excised and rearranged to provide DNA constructs encoding a desired tPA fragment.

The genetic constructs encoding the tPA analogues can be assembled and expressed by conventional recombinant DNA techniques. In general, DNA sequences are cleaved using restriction enzymes which are commercially available. The conditions of cleavage as to pH, time, temperature, concentration of enzyme are typically specified by the manufacturer. After each incubation, the enzyme is removed by extraction, for example, with phenol/chloroform and the nucleic acid fraction is recovered by precipitation with ethanol. Size separation of the cleaved fragments may be performed using standard agarose or polyacrylamide gel electrophoresis techniques as described in *Methods in Enzymology* (1980) 65:499–560. Fragments may be blunted if desired by treating with *E. coli* DNA polymerase I (klenow fragment) in the presence of the four deoxynucleotide triphosphates (dNTPs) using ambient temperature for about 30 minutes in 50 mM Tris.HCl pH 7.6, 50 mM NaCl, 6 mM $MgCl_2$, 6 mM DDT and 5–10 uM of the dNTPs. The extent of fill-in at the sticky ends may be, of course, regulated by appropriate choice of the dNTPs. Treatment under appropriate conditions with S1 nuclease removes single stranded portions.

Ligations are performed using T4-DNA ligase at pH 7.5 in Tris buffer, under conditions recommended by the manufacturer.

Construction of correct DNA sequences is confirmed by transforming *E.coli* or other suitable host, selecting successful transformants using the appropriate antibiotic resistance or other markers, and isolating plasmids from transformants, for example, by the method of Clewell, D., et al, *Proc Natl Acad Sci* (USA) (1969) 62:1159. Isolated DNA is analyzed by restriction enzyme mapping and/or sequencing. Sequencing uses either the dideoxy method of Sanger, F., et al, *Proc Natl Acad Sci* (USA) (1977) 74:5463, as further described by Messing, et al, *Nucleic Acids Res* (1981) 9:309 or by method of Maxam, et al, *Methods in Enzymology* (1980) 65:499.

Transformation of DNA vectors into *E. coli* or other prokaryotes is performed as described by Cohen, S. N., *Proc Natl Acad Sci* (USA) (1972) 69:110; for mammalian cells transformations are by the method of Graham and Van der Eb. *Virology* (1978) 52:546.

Alternatives and modifications of the foregoing methods are also employable, but the methods outlined above typify those useful in the construction of the DNA sequences encoding the tPA analogues and the synthetic tPA gene.

The DNA constructs encoding the tPA analogues can be expressed in prokaryotic expression systems. The preferred prokaryotic host is *E. coli*, although other bacterial strains such as Bacillus, Pseudomonas, or other Gram-positive or Gram-negative bacteria can also be used. A DNA construct encoding the desired tPA analogue is linked to control systems compatible with the host and disposed on a suitable DNA expression vector which is capable of replication in the host cell. The DNA expression vector comprises, in order, a promoter of bacterial or phage origin, a ribosome binding site, a translational initiation signal, the DNA construct encoding the tPA analog (see above), a translation termination site, and a terminator. Preferably, the vector also carries a gene encoding a selectable marker.

Common plasmid vectors include those derived from pBR322 and the pUC series. Charon 4 lambda phage is a frequently employed phage vector. Control sequences include promoter and ribosome binding site encoding sequences. A variety of such control sequences are available, most commonly the beta-lactamase (penicillinase) and lactose (lac) promoter systems (Chang et. al. *Nature* (1977) 198:106) and the tryptophan (trp) promoter system (Goeddel, et. al, *Nucleic Acids Research* (1980) 8:4057). Composite promoters containing elements of both the trp and lac promoter systems are also available. For the expression of $F_B$-CF and $F_B$-$F_B$-CF constructs the trp and tac promoters are preferred.

Eukaryotic microbes may also be used for expression of the analogues, most commonly laboratory strains of *Saccharomyces cerevisiae*, or Baker's yeast. A number of yeast control systems and vectors are available, including those which are promoters for the synthesis of glycolytic enzymes (Hess, et al. *J. Adv. Enzyme Req.* (1968) 7:149; Holland, et al, *Biochemistry* (1978) 17:4900). Yeast vectors employing the 2 micron origin of replication are suitable as transfer vectors (see, for example, Broach, J. R., *Methods Enzymol.* (1983) 101:307).

Tissue culture cell lines immortalized from mammalian or other higher organisms can also been used as recombinant hosts. Such cell lines include Chinese hamster ovary (CHO), Vero, HeLa, and Cos cells. In general, the Cos cell system is used for transient expression, while CHO cells typically integrate transformed DNA into the chromosome. Suitable mammalian vectors are generally based on viral origins of replication and control sequences Most commonly used are the simian virus 40 (SV40) promoters and replicon (Fiers, et al, *Nature* (1978) 273:113) and similar systems derived from Adenovirus 2, bovine papilloma virus, or avian sarcoma virus.

The tPA analogues expressed as heterologous protein in host cell systems can be purified and renatured by standard techniques for isolation and renaturation. Alternatively, an improved technique for isolation and renaturation of protein from *E. coli* cells as set forth below (and in further detail in the Exemplification), can be used. According to this technique, *E. coli* cells containing heterologous protein (tPA analogue) are lysed in a standard buffer and the cellular components are sedimented by, for example, centrifugation. The cells are resuspended and washed in a buffer containing 20–40% (preferably 25%) sucrose. The cells are then washed in a buffer containing 20–40% sucrose and a detergent such as deoxycholate. After the washes, the cells are sedimented, separated from the wash solution, resuspended in buffer and lysed in the presence of a protease inhibitor. Insoluble, heterologous protein (generally present in the form of inclusion bodies) is solubilized by extraction with a buffer containing a strong denaturant such as 2–8M urea (preferably 4M urea) or 6–8M guanidine.HCl. The protein is subjected to sulphitolysis and then renatured in a buffer containing reduced and oxidized glutathione in approximately a 10 to 1 molar ratio. The renatured protein can then be dialyzed to remove the denaturant. The renatured tPA analogue can further be purified by chromatographic steps such as gel filtration and/or affinity chromtography.

In addition to production by genetic engineering techniques, the tPA analogues can be synthesized by procedures of chemical protein synthesis such as the solid phase procedure of Merrifield.

The invention is illustrated further by the following exemplification.

Exemplification

I. Synthesis of tPA gene

The entire coding sequence for mature human tPA (shown in FIG. 2) was synthesized from three approximately equal-length gene fragments designated tPA1 (base pairs encoding the initiation site and amino acids 1–173), tPA2 (base pairs encoding and amino acids 174–346), and tPA3 (base pairs encoding amino acids 347–527 and stop codon). Each of these gene fragments was, in turn, constructed from oligonucleotide subunits. tPA1 required the synthesis of 70 oligonucleotides de novo: the entire tPA gene required the synthesis of 215 oligonucleotides.

a. Chemical Synthesis of Oligonucleotides

The chemical synthesis of the 215 oligonucleotides was accomplished by two methods: phosphotriester (ca. 50% of the fragments) (Crea and Horn, *Nucl. Acids Res.*, 8, 2331, 1980) and phosphite triester method (Alvarado-Urbina et al., *Science* 214, 270, 1981).

Described below is a typical oligonucleotide synthesis by the phosphite method, involving the use of automatic synthesizer and the "in situ" activation of the phosphite nucleotide intermediates. The phosphite method is the method of choice, being suitable to automation.

Materials and Methods

Anhydrous acetronitrile and 2,6 lutidine were prepared by distillation from calcium hydride and stored over activated molecular sieves. The 5'-DMT-N-protected deoxyribonucleosides were prepared by standard methods and lyophilized from 1,4 dioxane prior to use. Chlorodiisopropylaminomethoxy phosphine was purchased from American Bionuclear.

In situ preparation of phosphoramidites

In a typical preparation, an oven-dried septum bottle was charged with 10 ml of anhydrous acetonitrile, 0.6 ml of 2,6 lutidine and 0.2 ml of chloro-N, N-diisopropylamino phosphine. A 1 mmol portion of lyophilized 5'-DMT-N-protected deoxyribonucleoside was dissolved in 5 ml of anhydrous acetonitrile and injected into the reaction vessel. The nucleoside vial was washed with an additional 5 ml of acetonitrile and the wash solution was injected into the reaction vessel. The reaction mixture was stirred for 10 minutes at ambient temperature and activated by the addition of a solution containing 210 mg of 1H-tetrazole in 30 ml of anhydrous acetonitrile. Phosphoramidite solutions prepared in this manner have been used over time periods exceeding 12 hours with satisfactory results.

Oligonucleotide Synthesis

Oligonucleotide synthesis was carried out on a silica solid support using the automated synthesizer described below. A standard cycle consisted of the following 10 min, stop-flow protocol:

| Reagent | |
| --- | --- |
| Phosphoramidite | 01:00 |
| Stop Flow | 01:00 |
| Oxidation* | 00:30 |
| Pyridine Wash* | 01:30 |
| Methylene Chloride Wash | 01:30 |
| DMT Deblock** | 01:30 |
| Methylene Chloride Wash | 01:00 |
| Acetonitrile Wash*** | 02:00 |

Flow rate = 5 ml/min
*1% $I_2$ in 3:1:1 THF:pyridine:$H_2O$
**3% Trichloroacetic acid in $CH_2Cl_2$
***Dried 24 hr in over activated molecular sieve

Automated Synthesizer

The instrument consisted of a series of pneumatic three-way valves, 120 v solenoids and a pump. Solenoid operation was effected via BSR-X10 switches under control of a Commodore 64 computer equipped with a VIC controller (Genesis Computer Corporation). The minimum configuration required by the protocol described above would utilize 10 valves, 5 solenoid units and 10 BSR switches. We have enhanced the capability of the instrument by the addition of valves to provide for on-line catalyst mixing, recycling of reagents, collection of DMT solution during deblocking and multicolumn sequential synthesis.

The control software was written in BASIC and utilized a machine language subroutine to effect valve operation. The menu-driven software allowed for creation and storage of various synthesis protocols, completely automated synthesis, and full manual override of all functions. Protocols were created in response to machine prompts and allowed the use of phosphotriester or phosphite methods as well as on-column phosphitylation of the growing oligonucleotide. Additionally, the ability to run in a stop-flow mode allowed the use of smaller quantities reagents than required in continuous flow operation. The synthesis subroutine prompts the use to input the desired protocol, sequence, and other data required for printout of production records. At any time during the synthesis, the user may escape to the manual overide subroutine, operate any of the valves and return to the synthesis.

Workup and Purification

Oligonucleotide cleavage and deprotection was effected by the standard two-step procedure consisting of treatment with 2:1:1 dioxane/triethylamine/thiophenol, followed by overnight treatment with concentrated ammonia at 55° C. The resulting solution was evaporated to dryness and dissolved in 1 ml of 3:1 water/ethanol.

Purification was carried out by streaking. 0.15 ml of the crude oligonucleotide solution on a 20×20 cm Kieselgel 60 TLC plate and eluting with 5.75:3.25:10 n-propanol/concentrated ammonia/water. The product band was visualized under UV, scraped from the TLC plate and eluted with 3:1 water/ethanol. The purified oligonucleotides were checked for the correct size homogeneity by gel electrophoresis of 0.05 OD sample on polyacrylamide gel with 0.5X TBE buffer and 7M urea. The gel was stained with ethidium bromide and visualized under UV light. Following phosphorylation with T4 kinase, all possible pairwise ligations were tested at 37° C. for 30 min. Positive results from these ligation tests were taken as partial confirmation of sequence pending sequence analysis of the assembled gene. Synthesis, purification and quality control was similar for all 215 oligonucleotides. Fragments that failed to pass purity and size tests were resynthesized and purified as above.

b. Gene Ligation

Figure 3:
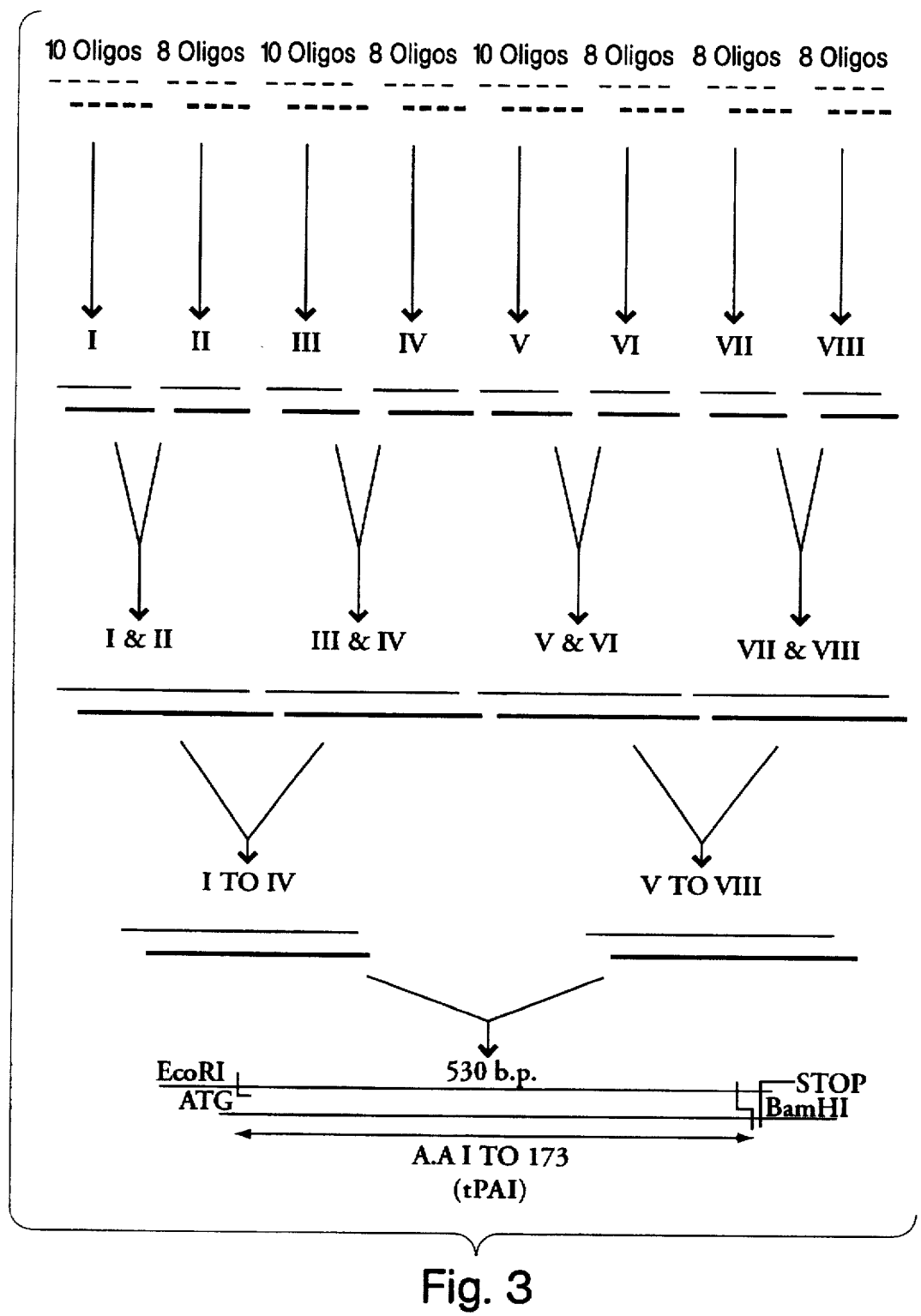
FIG. 3 is a schematic representation of the synthesis and ligation of the tPA 1 gene from precursor oligonucleotides.

The three genes, tPAI, II, and III were obtained by the enzymatic ligation (DNA-ligase) of oligonucleotides, each using a similar ligation approach. The general scheme of tPAI gene ligation is shown in FIG. 3.

The tPA I gene was constructed from 70 oligonucleotides. Eight large gene fragments, I to VIII, were synthesized from oligonucleotides by 5' phosphorylation followed by enzymatic ligation. Phosphorylation was carried out at 37° C. for 1 hr in a reaction mixture containing oligonucleotides (1.2 ug of each), 1 mM ATP, T4 phosphorylase kinase (1.3 units/ug DNA), 70 mM Tris.HCl, pH 7.6, 10 mM $MgCl_2$, and 5 mM dithiothreitol. Ligation of the phosphorylated oligonucleotides was carried out at 15° C. for 2 hr in a reaction mixture containing 0.075 mM ATP, T4 DNA ligase (1.5 unit/ug DNA), 50 mM Tris.HCl, pH 7.8, 10 mM $MgCl_2$, 20 mM dithiothreitol, and 50 ug/ml BSA. The DNA fragments were resolved by electrophoresis on 8% polyacrylamide gels in the Trisborate-EDTA buffer system described by Maniatis et al. (*Proc. Natl. Acad. Sci. USA*, 72,1184, 1975). Bands migrating at the expected molecular weight were sliced from the gel and were electroeluted using published techinques (Maniatis et al., "Molecular Cloning", Cold Spring Harbor Laboratory, N.Y., 1982). The eluted DNA was dried under vacuum and was resuspended in 200 ul of 0.2M sodium acetate, pH 5. The sample was extracted twice with equal volumes of phenol, chloroform, and isoamyl alcohol (50:50:1), and once with chloroform. The DNA was precipitated with 2.5 volumes of absolute ethanol. The purified gene fragments were stored at 4° C. in 1 mM Tris.HCl, pH 7.5, and 0.1 mM EDTA.

Stoichiometric amounts of gene fragments I to VIII (5.4 ug total) were combined and ligated using the conditions described above. After gel electrophoresis, the DNA band that migrated at 530 base pairs was sliced from the gel, electroeluted, and purified as described above.

c. Molecular Cloning

The synthetic tPAI gene was inserted into the EcoRI and BamHI sites of pUC8 (Viera and Messing, *Gene*, 19, 259, 1982). pUC8 (6 ug) was digested at 37° C. in a 40 ul reaction mixture containing BamHI (32 units), 6 mM Tris.HCl, pH 7.9, 6 mM $MgCl_2$, 150 mM NaCl, and 3 mg/ml BSA. After one hour, 6 ul of 1M Tris. HCl, pH 7.5, and 40 units of EcoRI were added to the digestion mixture. The volume was adjusted to 60 ul with sterile water, and the digestion was allowed to proceed at 37° C. for an additional hour. The DNA fragments were resolved by electrophoresis on a 6% polyacrylamide gel. The large fragment was sliced from the gel and was electroeluted. The synthetic tPA in gene (30 ng) and the large EcoRI/BamHI fragment of pUC8 (100 ng) were combined and treated with T4 DNA ligase. The ligation mixture was used to transform competent *E. coli* K12 JM83 cells. Competent cells were prepared by using the calcium chloride method described by Maniatis et al. supra. Transformants were selected by plating on LB agar (Maniatis et al., supra) containing 50 ug/ml ampicillin. Plasmids were isolated from small cultures of transformed bacteria by using a modification of the method of Birnboim and Doly (*Nucl. Acids Res.*, 7, 1513, 1979) as described by Maniatis et al., supra. Purified plasmids were screened for the presence of the 530 base pair tPAI gene insert by polyacrylamide gel electrophoresis after digestion with EcoRI and BamHI . Large scale preparations of plasmids containing the tPAI gene insert were carried out by using the alkaline lysis method of Birnboim and Doly, supra.

d. DNA Sequence Analysis

The DNA sequence of the cloned tPAI gene was determined by the dideoxy chain termination method (Sanger et al., *Proc. Natl. Acad. Sci. USA*, 74, 5463, 1977). pUC8 plasmid containing the gene was cleaved with EcoRI and BamHI, and the gene insert was purified by gel electrophoresis. The tPAI gene was inserted into the EcoRI and BamHI sites of M13 mp 18 and mp 19 (Messing, supra). Single stranded M13 templates were prepared by using the method of Schreier and Cortese (*J. Mol. Biol.*, 129, 169, 1979).

e. Verification of the Synthetic Gene Sequences

The sequencing of the synthetic gene was done on the 6 fragments that were used as building blocks of the tPA gene; thus, errors were eliminated before the whole molecule was completely assembled. A second sequencing analysis was performed after completion of the construction in order to assure that no deletions had occurred during the multiple steps of assembly. While the shorter fragments can be directly sequenced after cloning into the master cloning sites of the m13 phage genome using the m13 oligonucleotide primer to initiate the polymerase reaction, the whole gene is too large to be sequenced in one reaction. Therefore, internal primers were used that had been chosen from oligonucleotides of tPA retained from the synthesis of the gene and spaced at appropriate intervals. These intervals were approximately 250 bps which allowed sufficient overlapping of the sequences.

In addition to the sequencing analysis, the reading frame of the initial fragments and combinations of adjacent fragments were tested by direct expression in *E. coli* and the immunoreactivity of the resulting polypeptides was analyzed. While single base deletions could potentially be over-looked during sequencing they would cause a change in reading frame for the translation of protein. Consequently, an alteration in polypeptide size in conjunction with a loss of antigenic determinants would be observed. These tests provided valuable insights into the expression behavior of various domains of the tPA molecule and confirmed the reactivities of the antisera being used.

II. Expression of tPA Analogues in *E. coli*

Construction of Expression Vectors

Figure 4:
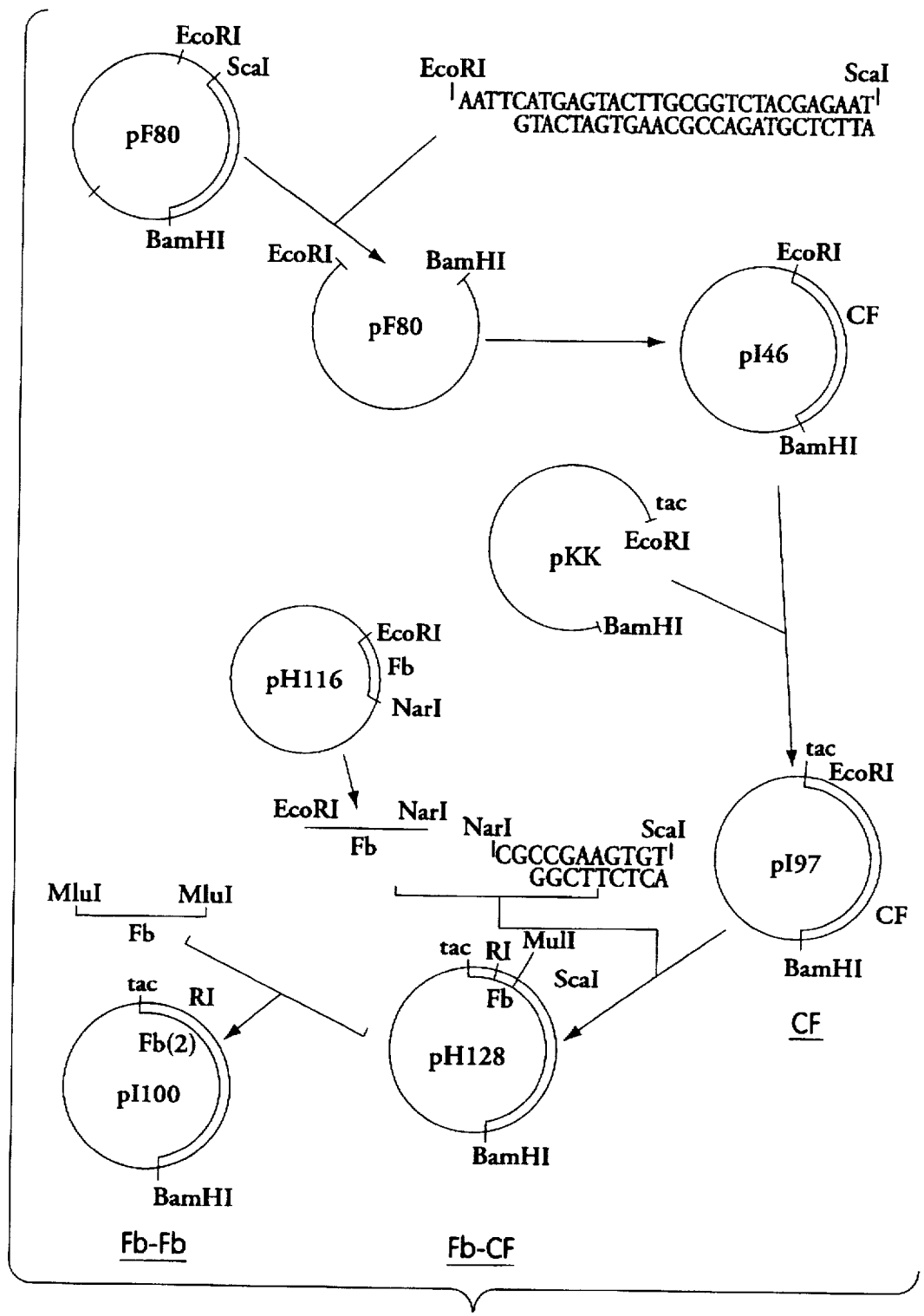
FIG. 4 is a schematic for construction of expression vectors containing $F_B$-$CF_{tPA}$ and $F_B$-$F_B$-$CF_{tPA}$ gene constructs.

The construction of the plasmid for the direct expression of catalytic fragment was facilitated by the ligation of a ScaI to BamHI fragment from pF80, a plasmid which contained the entire tPA gene, and a synthetic EcoRI to ScaI DNA to a cut pUC plasmid to form pI46. The resultant CF gene, an EcoRI to BamHI fragment was inserted into a pKK expression vector to form pI97. The catalytic fragment was directly expressed under the control of the tac promoter (FIG. 4). To synthesize the $F_B$-CF fusion protein, an EcoRI to NarI fragment, containing the $F_B$ nucleotide sequences and isolated from pH116, and a synthetic NarI to ScaI linker were inserted into pI97 cut with the restriction enzymes, EcoRI and ScaI (FIG. 4) to form pH128. The use of the synthetic linker deleted the initiation codon and joined the $F_B$ polypeptide directly to the first amino acid (ser) of the catalytic fragment. The $F_B$ dimer catalytic fragment ($F_B$-$F_B$-CF) was constructed by opening the $F_B$-CF gene at the unique MluI site in the $F_B$ coding region and inserting an MluI fragment derived from a dimer of $F_B$ coding sequences (FIG. 4) to form pI100. To construct for the expression of $F_B$-$X_a$-CF, a synthetic NarI to ScaI DNA fragment was inserted into pI46, which was a plasmid containing the gene for the catalytic fragment, to form pP1. Both the NarI to BamHI fragment, isolated from pP1, and the EcoRI to NarI fragment, containing the $F_B$ coding sequences from pH116, were ligated into pI46, opened at both the EcoRI and BamHI sites to form pP4. To express the $F_B$-$X_a$-CF, the complete gene was isolated in two DNA fragments: EcoRI to SacI and ScaI to PstI nucleotide sequences. These two fragments were inserted into a pKK expression vector as pP5 under the control of the tac promoter.

To construct the tPA analogue containing the hybrid kringle, the NarI to NarI fragment in the two kringle regions was deleted. In order to delete this fragment, two DNA fragments: the EcoRI to NarI and the NarI to BamHI nucleotide sequences were ligated into pUC8 after digestion by restriction enzymes EcoRI and BamHI. The resultant gene was then isolated in two pieces, an EcoRI to HindIII fragment, and a HindIII to PstI fragment and inserted into the expression vector to be fused with the trp leader by a three-factor ligation. The tPA analogue containing only one kringle region was constructed by deleting the second kringle. The vector was pUC with tPA 1.23, cut at SphI and BamHI, dropping out tPA2 and tPA3. A fragment containing part of tPA2 was isolated between PstI (at 789 bps) and BamHI (at 1051 bps). These fragments were ligated after addition of two strands of synthetic DNA, CBM#2014 and CBM#2015. The resulting construct is deficient of the tPA 3 domain.

In the next contruction step, the single kringle analog was completed by combining in pUC a fragment, bearing only the first kringle, spanning from EcoRI (at 1 bps) to AvaI (formerly at 1042 bps), and another fragment containing tPA3 from AvaI (1042 bps, partial digest) to SalI (1599 bps).

Competent *E. coli* K12 RB791 were mixed on ice with 50 ng of the tPA encoding plasmids for 30 min followed by heat shock at 40° C. for 2–3 min and then grown on 1 ml LB medium without antibiotics for 30 min. The cells were spun down and resuspended in 100 ul LB medium, and then transferred to agar containing 20 ug/ml tetracycline. Resistant colonies were picked, grown in LB medium, and induced by the addition of 10 g/ml indole acrylic acid (IAA).

To assay for the expression of protein, the cells were harvested 5–10 hours after induction and the cell paste was dissolved in 6M guanidine. HCl containing 25 mMTris.HCl buffer, pH 8.0, 0.15M NaCl, mM EDTA, and sonicated briefly. The sonicate was dialyzed vs the same buffer without guanidine. Aprotinin (10 units/ml) was added during during dialysis to protect the protein from *E. coli* serine proteases.

To assess biological activity, a fibrinolytic assay was conducted on each crude extract before and after dialysis; cells without DNA encoding the catalytic region of tPA showed no fibrinolytic activity. Thus, fibrinolysis could not be attributed to nonspecific proteases in the *E. coli* extract.

Preparation of Inoculum for Bacterial Fermentation

A frozen *E. coli* stock containing the desired plasmid was inoculated into 200 ml of LB broth, containing 10 g/l tryptone, 5 g/l yeast extract, 5 g/l NaCl and 1 ml/l of a tetracycline stock (10 mg/ml of 95% ethanol and 5% isopropanol) in a 1 liter baffled shaker flask. The culture was incubated on a rotating platform at 200 rpm for 17 hours at 37 C.

Fermentation of *E. coli*

The overnight culture was inoculated into 10 liters of 1 g/l $Na_2HPO_4 \cdot 7H_2O$, 8 g/l glucose, 5 g/l caesin hydrolysate, 5 g/l NaCl, 3 g/l $KH_2PO_4$, 1 g/l $NH_4CL$, 1 ml/l 1M $MgSO_4$, 0.5 ml/l 1% trytophan in glacial acetic acid, 0.1 ml/l 1M $CaCl_2$, 1.5 ml/l of a trace mineral mix (27 g/l $FeCl_3 \cdot 6H_2O$, 1.3 g/l $ZnCl_2$, 2 g/l $CoCl_2 \cdot 6H_2O$, 2 g/l $NaMoO_4 \cdot 2H_2O$, 1 g/l $CaCl_2 \cdot 2H_2O$, 1.3 g/l $CoCl_2 \cdot 2H_2O$), 0.5 g/l $H_3BO_3$ and 100 ml of concentrated HCl) and 2 ml of 10 mg/ml tetracycline, pH 7.0 in a 14 liter fermentor. The bacterial culture was agitated at 300 rpm and incubated at 37 C. The pH of the culture medium was maintained in the range of 6.85 to 7.15 by the addition of either a solution of 10% phosphoric acid or a stock of 1M $NH_4OH$. The culture was sparged with air at a flow rate of 10 liter per min.

When the desired cell density for the bacterial culture containing an expression vector under the control of the tac promoter was reached, isopropyl-thiogalactopyranoside was added to a final concentration of 0.1 mM. After induction, the pH controller was turned off and the fermenation was allowed to proceed until the pH of the medium increased to 7.4.

Cell Recovery

At the end of the fermentation, 10 liters of the bacterial culture were decanted into a 20-liter carboy. An Amicon hollow fiber ultrafiltration unit was used to concentrate the culture medium down to 1.5 l. The bacteria were pelleted in 500 ml bottles by centrifugation at 6000 rpm for 10 min. After decanting the supernatant, the cell pellet was transferred to 50 ml capped tubes and stored at −70 C. until use.

Preparation of inclusion bodies from *E. coli*

After fermentation, 1 gm of wet cell paste was suspended in 10 ml of 25% sucrose in 25 mMTris.HCl, 10 mM EDTA, 0.1M NaCl, pH 8.0. The cells were incubated on ice for 10 minutes and the cell suspension was centrifuged at 8000 rpm for 10 min at 4 C. in a Beckman refrigerated J21-B centrifuge. After decanting the supernatant, the cell pellet was resuspended in 10 ml of 25% sucrose in 25 mM tris-HCl, 10-mM EDTA, pH 8.0. Addition of 5% of detergent to the wash resulted in removal of a greater number of contaminating proteins from the inclusion bodies. After incubation on ice for 10 minutes, the cells were centrifuged at 8000 rpm for 10 minutes. After removing the supernatant, the cell pellet was resuspended in 10 ml of 25 mM Tris.HCl, pH 8.0 and again incubated on ice for 10 minutes. 20 KIU per ml of aprotinin or 0.5 mM PMSF was added to the cell preparation to inhibit protease. To lyse the cells, 1 mg of lysozyme was added to the cell suspension and mixed by vortexing. After incubation on ice for 5 minutes the cells were broken by sonication, 3×1 minute bursts separated by 1 minute intervals. Then, the inclusion bodies and cell debris were pelleted at 17,000 rpm for 20 minutes at 4 C. The inclusion body preparation was be stored at −80 C. or used immediately.

Solubilization of protein

Protein can be sequentially extracted from the inclusion body preparation by resuspension into 10 ml of 25 mM Tris.HCl, 10 mM EDTA, pH 8.0; 10 ml of 25 mMTris.HCl, 10 mM EDTA, containing 1% Triton X-100 or 0.5% sodium deoxycholate; 10 ml of 25 mM Tris.HCl, 10 mM EDTA, pH 8.0, containing 2 to 4M urea; 10 ml of 25 mM Tris.HCl; 10 mM EDTA, pH 8.0, containing 6 to 8M guanidine. HCl; and finally 10 ml of 25 mM Tris.HCl, 10 mM EDTA, 6–8M guanidine.HCl , 1% B-mercaptoethanol, pH 8.0.

Sulfitolysis and renaturation

Protein solution was diluted into 6 to 7M guanidine.HCl, 25 mM Tris.HCl, 10 mM EDTA, pH 8.0, containing 20 mg/ml sodium sulphite and 10 mg/ml sodium tetrathionate. The optimal protein concentration for sulphitolysis was determined to be 125 ug/ml. The protein solution was incubated at room temperature for at least 15 hours. Then, the protein was diluted into a renaturation buffer consisting of 25 mM Tris.HCl, 10 mM EDTA, 0.01% tween, 1M guanidine. HCl, mM reduced glutathione and 0.1 mM oxidized glutathione, pH 8.3 to 8.5. The renaturation of protein was allowed to proceed at 22 C. for 7 to 24 hours. After renaturation, the guanidine-HCl has to be removed immediately by dialysis to retain the biological activity.

Purification of the refolded catalytic fragments

Both $F_B$-CF and $F_B$-$F_B$-CF were partially purified by immunoaffinity chromatography on a PAM-2 column (American Diagnostica, Conn). PAM-2 is a monoclonal antibody specific for two-chain melanoma tPA(mtPA). 10 mg of antibody were coupled to 1.5 ml of CNBr activated sepharose 4B. About 1 to 2 mg of refolded catalytic fragments were allowed to pass through the column at a flow rate of less than 30 ml per hour at room temperature. Adsorption of the catalytic fragments to the immobilized antibody could also be facilitated by incubating the protein with the beads overnight at 4 C. on a rotating platform. The column was then washed with 10 bed volume of 20 mM Tris.HCl, 0.1M NaCl, pH 7.5. The bound protein was then eluted sequentially with 0.25M KSCN and 1.5M KSCN in 20 mM Tris.HCl, pH 7.5. Protein elution profile was monitored by a chromogenic assay using substrate S-2251 before or after extensive dialysis against 0.5 mM Tris.HCl, pH 7.5 at 4 C. After dialysis, the protein concentration was determined by Bio-rad protein assay using bovine serum albumin as a standard.

Biological Assay of tPA and catalytic fragments
Fibrin plate assay

A 0.5% plasminogen-rich bovine fibrinogen solution was prepared by dissolving the fibrinogen powder (75% clottable, Miles Scientific) in 50 mM Tris.HCl, 90 mM NaCl, 0.01% sodium azide (optional), pH 7.5, at 37 C. The fibrinogen was then cooled to 4C. by incubation on ice. To 10 ml of the cooled solution, 0.18 ml of a 20 U/ml bovine thrombin solution (CalBiochem) was added. Immediately after the thrombin was thoroughly mixed with the fibrinogen, the solution was poured onto an assay plate. The fibrinogen was allowed to clot at room temperature for about 30 minutes. To assay for the biological activity of the catalytic fragments, 10 ul of sample after diluted 1:1 with 0.25% swine gelatine (Sigma) in 50 mM Tris.HCl, 90 mM NaCl and 0.1% Tween 80. The plate was incubated at 37 C. overnight. Relative biological activity of the samples corresponds to the diameter of the lytic zone around the sample. Urokinase or mtPA served as the reference. The sensitivity of the assay is in the range of 0.62 to 20 U/ml.

Chromogenic assay

About 1 to 4 ul of the sample was mixed with 30 ul of 10 mM Tris.HCl, 0.1% Tween 80, 12.5 m units of plasminogen, 0.78 mg plasminogen-free fibrinogen, pH 7.5, and incubated in a 37 C. water bath for 10 minutes in a 96-well microtiter plate directly or in 1.5 ml Eppendorf tubes. Then, 70 ul of 0.5 mM chromogenic substrate, S-2251 (Kabi Vatrum, Sweden) were added to the reaction mixture followed by incubation for another 30 minutes. The reaction was stopped by the addition of 10 ul of 50% glacial acetic acid. The color developed was recorded in a plate-recorder at A405. Melanoma-tPA (American Diagnostica) calibrated by the international standard from the National Bureau of Standard (London, UK) was used as a standard. The sensitivity of the assay is in the range of 5 to 25 u/ml.

Binding of $F_B$-$F_B$-CF analogue to fibrin

Figure 6:
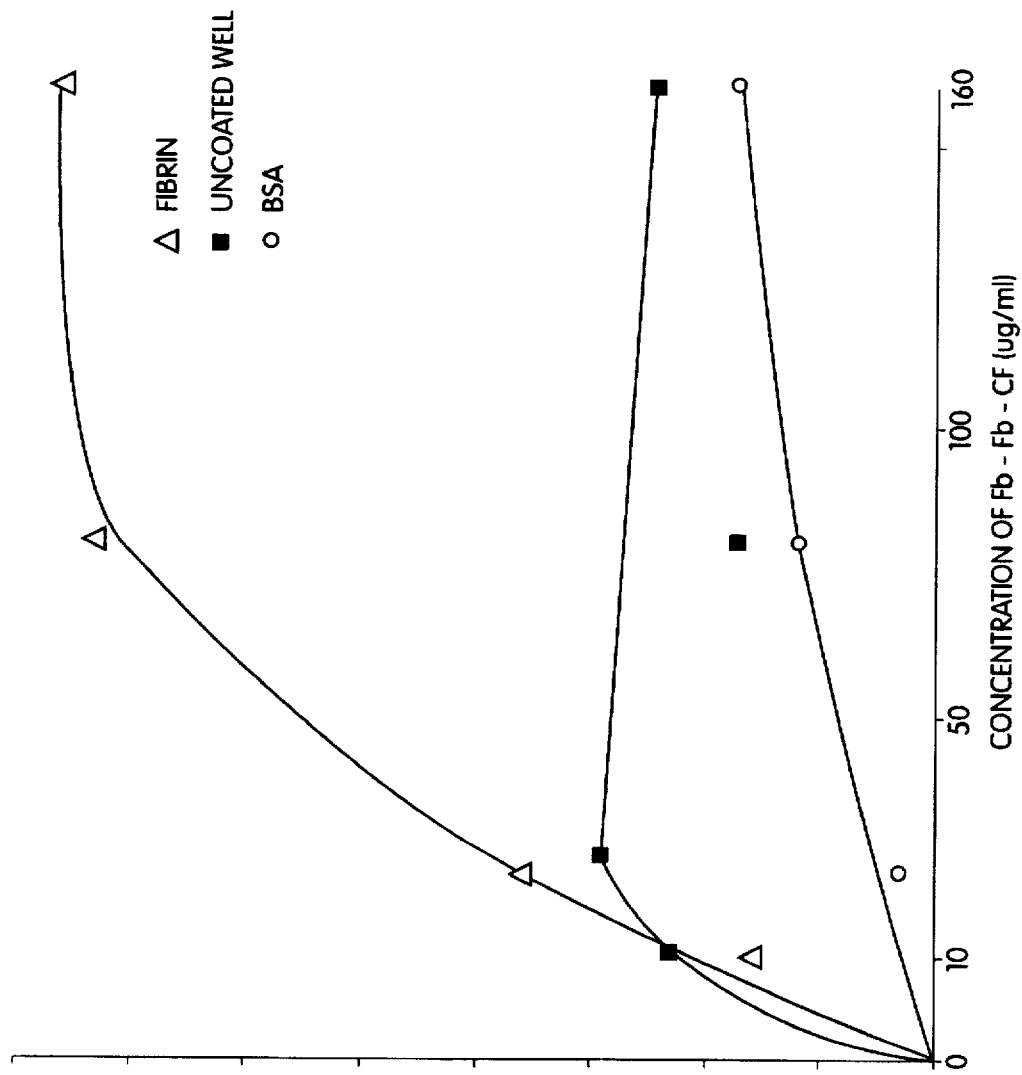
FIG. 6 shows the results of a fibrin binding assay for $F_B$-$F_B$-$CF_{tPA}$ analogue.

Wells were coated with fibrinogen or bovine serum albumin (BSA) by drying 200 ul of a 10 mg/ml solution in a 96-well plate. The fibrinogen was then converted into fibrin by incubation with 4 munits of thrombin in 100 ul of phosphate buffered saline, pH 7.2 (PBS) at 37 C. for 1 hour. Various quantities of $F_B$-$F_B$-CF, as indicated in FIG. 6, were then added to the well in 100 ul PBS and incubated at 37 C. for 2 hours to facilitate binding. After incubation, the supernatant was removed and the wells were then washed once with 100 ul PBS. The amount of bound and unbound $F_B$-$F_B$-CF were determined by chromogenic assay.

Molecular weight determination by zymographic analysis

The molecular weights of the active catalytic fragments were estimated by zymographic analysis. An 11% SDS polyacrylamide gel containing 0.1% gelatin and 1.5 units of plasminogen was prepared. Electrophoresis was allowed to proceed at 4 C. for 3 to 4 hours, at 10 mamp per gel. Then, the gel was incubated with shaking at room temperature in 2.5% triton X-100 to remove the SDS in the gel so as to restore the biological activity of the catalytic fragments. The gel was then incubated in 0.1M glycine.HCl, pH 8.3 at 37° C. for 3 hours. After the incubation, the gel was stained with Bio-rad protein reagent diluted 1:8 with deionized $H_2O$.

RESULTS

Preparation of inclusion bodies

The first wash of the cells with hypertonic solution (25% sucrose) collapsed osmotically the inner membrane, thereby releasing a large number of cellular proteins, especially when the expression level of the catalytic fragments was high. The choice of detergent used in the second wash depended on the solubility of the catalytic fragment. Cells expressing the trp-CF, the least soluble catalytic fragment, were washed with 1% dodecyl sulphate without solubilizing the inclusion bodies. However, the protein in the inclusion bodies could be solubilized under the same conditions when they are purified from the cells. Cells expressing other catalytic fragments cannot withstand this treatment. A weaker detergent, such as 1% Zwittergent 3–16 (Z-16) or deoxycholate was used without solubilization of the inclusion bodies before lysis of the cells. Deoxycholate has an added advantage over the other detergent in that it is dialyzable. The prewash with detergent before lysis of the cells removed considerable amounts of contaminating proteins.

Solubilization of catalytic fragments

Various analogues of catalytic fragments exhibit differences in solubility. Of all the catalytic fragments studied, the solubility in aqueous buffer decreases in the order of $F_B$-$F_B$-CF>$F_B$-CF>CF>trp-CF. The varying degree of solubility can be attributed to the leader sequences of the molecules. Of the two denaturants used to recover protein from inclusion bodies, i.e., urea or guanidine.HCl, both proved to be satisfactory. In the case of urea extraction, 4M was determined to be the optimal concentration. 2M urea did not result in recovery of all the desired protein; while extraction with 8M urea resulted in a high degree of contamination with the other cellular proteins. After extraction, the urea was removed completely by dialysis against Tris. HCl buffer without precipitating any proteins. However, when proteins were extracted with 6–8M guanidine.HCl, precipitation of proteins occurred when the guanidine.HCl was removed directed by dialysis.

Renaturation of the catalytic fragment

To reduce intermolecular crosslinking of the protein in solution during renaturation, the concentration of protein was generally maintained low. In order to obtain maximum yield of properly folded protein, the concentration of protein was kept at 1 ug/ml in the presence of 1M guanidine.HCl after sulphitolysis.

During renaturation of sulphonated proteins, a low concentration of denaturant was required. Maximal refolding of protein as indicated by the highest biological activity observed when the guanidine.HCl concentration was in the range of 0.6M to 2M, above or below which the yield of properly refolded protein dropped precipitously.

The total concentration of glutathione and the ratio of the reduced and oxidized forms influenced dramatically the rate of protein renaturation. The higher the glutathione concentration, the faster was the rate of refolding. The time to reach maximal refolding was reduced from 7 to 1 or 2 hours when the total glutathione concentration was increased from 1.1 mM to 11 mM. However, in order to recover maximum yield of properly folded protein, the concentration of glutathione was kept at 1.1 mM. In refolding sulphonated proteins, maximal refolding was achieved when the ratio of the reduced to the oxidized form of glutathione is maintained at ten.

During sulphitolysis, the effect of sodium sulphite and sodium tetrathionate concentrations on the rate of renaturation was analyzed. The optimal concentration of sodium sulphite and sodium tetrathiohate was observed to be 20 mg/ml and 10 mg/ml respectively.

Temperature, in general, did not influence the rate of refolding of the catalytic fragments drastically. All the refolding experiments were carried out at room temperature. The optimal pH of the refolding after sulphitolysis was from 8.3 to 8.5.

The addition of non-ionic detergent to the refolding solution has been indicated to disperse the proteins so as to increase the yield of properly folded proteins. However, in all the experiments carried out, the data supported the fact that the addition of non-ionic detergent during folding is not necessary.

Purification of renatured catalytic fragment

Partial purification of $F_B$-CF and $F_B$-$F_B$-CF can be achieved by immunoaffinity chromatography (PAM-2). PAM-2 is a murine monoclonal antibody which will reacts with the two-chain m-tPA with a binding constant of M. After chromatography, a ten-fold increase in specific activity of $F_B$-$F_B$-CF can be achieved. Presumably, the column can selectively enrich biologically active molecules. On the other hand, no enhancement in specific activity of $F_B$-CF can be achieved by the PAM-2 chromatography.

Analysis of the partially purified $F_B$-$F_B$-CF and $F_B$-CF by SDS polyacrylamide gel electrophoresis indicated single bands of proteins at 41,000 and 31,000 daltons respectively. The protein is essentially pure because little or no contaminating bands are observed.

Characterization of recombinant tPA and analogues

The effect of plasminogen and fibrinogen on the activity of the catalytic fragments was determined (Table 1).

In the absence of plasminogen, no biological activity was detected. This indicates that the catalytic fragments are, indeed, plasminogen activators because they are plasminogen-dependent for activity.

Potentiation of the activity of natural tPA by fibrinogen has been clearly indicated. When compared to mtPA, potentiation the activity of $F_B$-CF and $F_B$-$F_B$-CF by fibrinogen is less dramatic.

The biological activity of $F_B$-CF and $F_B$-$F_B$-CF can be completely neutralized by incubation with polyclonal antibody against mtPA. This suggests that all the recombinant molecules are tPA analogues.

TABLE 1

Effect of Plasminogen and Fibrinogen on the Activity of tPA and Catalytic Fragments

| Biological | complete[1] | -fibrinogen | -plasminogen | Potentiation[2] by fibrinogen |
|---|---|---|---|---|
| $F_B$-$F_B$-CF | 12.5 | 6.0 | 0 | 2.7 |
| $F_B$-CF | 67.5 | 35.0 | 0 | 1.8 |
| mBtPA | 96.0 | 7.0 | 0 | 8.2 |
| urokinase | 39.0 | 42.0 | 0 | 0 |

[1]The plasminogen activator was incubated with both fibrinogen and plasminogen.
[2]The potentiation of tPA activity by fibrinogen was estimated by the ratio of the tPA activity in the presence and absence of fibrinogen. Each number represents the average of a minimum of two separate experiments.

The molecular weights of tPA and the catalytic fragments were estimated by zymographic analysis. The molecular weights of recombinantly produced tPA (rtPA) CF, $F_B$-CF and $F_B$-$F_B$-CF were estimated to be 71,000, 27,500, 31,000 and 41,000 daltons respectively.

Binding to fibrin

Figure 7:
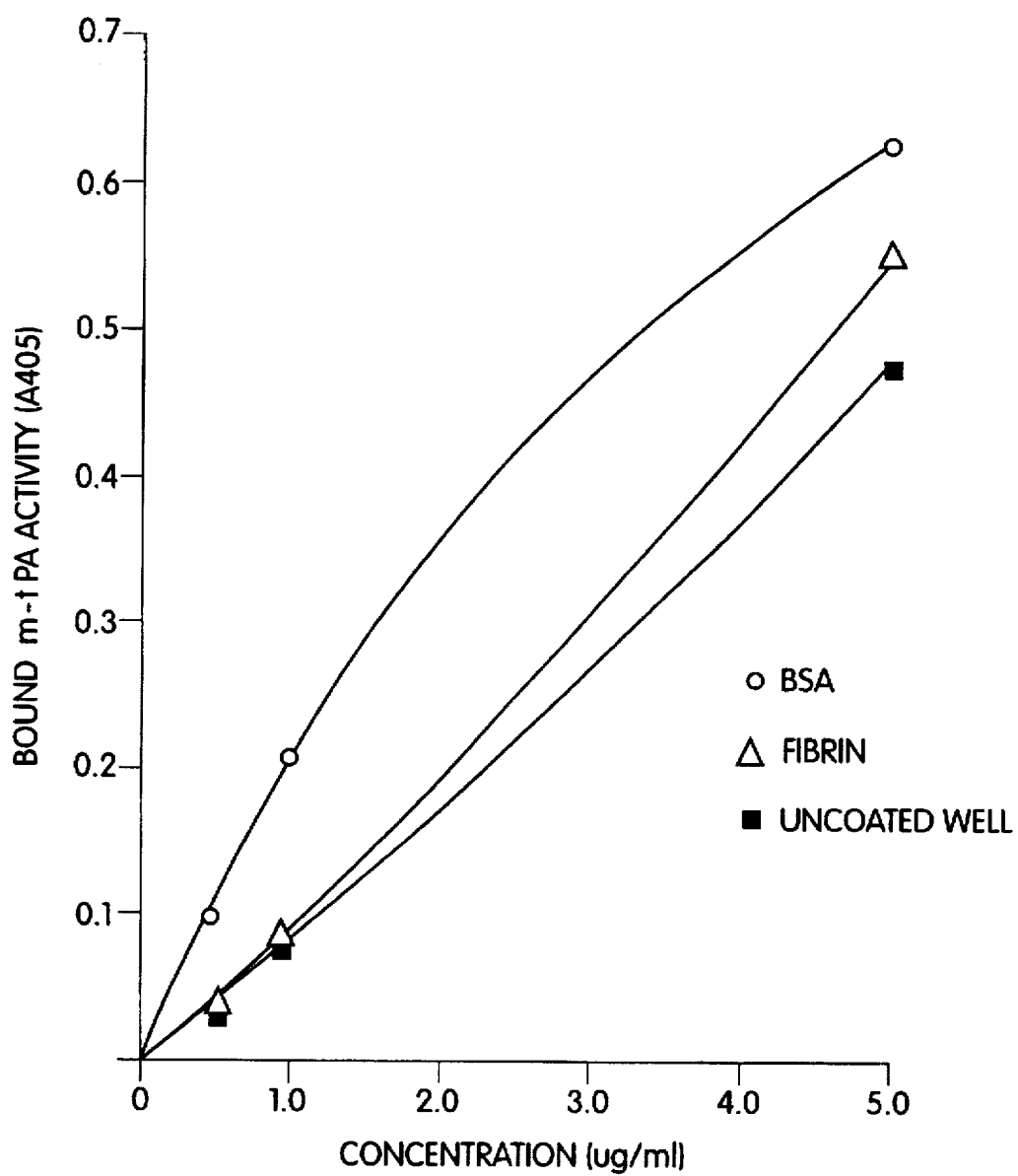
FIG. 7 shows the binding of mtPA to fibrin.

FIG. 6 indicates the extent of binding of $F_B$-$F_B$-CF to fibrin immobilized on microtiter plates. In contrast, much less $F_B$-$F_B$-CF binds to bovine serum albumin. In fact, BSA inhibits the non-specific binding of $F_B$-$F_B$-CF to the uncoated well of the 96-well plate. In addition, $F_B$-$F_B$-CF binds equally well to fibrinogen when compared to fibrin. In order to ascertain whether $F_B$-$F_B$ is, indeed, the moiety responsible for the binding of $F_B$-$F_B$-CF to fibrin, a $F_B$ tetramer was used to compete for binding. A molar ratio of 40 to 1 ($Fb_4$ to analogue) inhibited completely the ability of $F_B$-$F_B$-CF to bind to fibrin. In addition, the fact that iodinated $F_B$ tetramer binds to both fibrin and fibrinogen also substantiates that the binding domain of the $F_B$-$F_B$-CF to fibrin resides on the $F_B$-$F_B$ moiety of the molecule. On the other hand, melanoma-tPA, a very hydrophobic molecule, binds equally well to fibrin, BSA and the uncoated wells (FIG. 7). Therefore, it is not possible to assess the binding capability of tPA to fibrin under these experimental conditions. These results also suggest the $F_B$-$F_B$-CF is less hydrophobic than the natural tPA molecules.

Industrial Applicability

The tPA analogues of this invention are useful as thrombolytic agents. For this purpose, the tPA analogues can be formulated into injectable, thrombolytic compositions. A purified tPA analogue can be mixed with a conventional excipient for injection, e.g., a buffer, a filler, a stabilizer or the like. Preferably the analogues are administered intravenously; however, analogues comprising $F_B$ domain of protein A linked to a catalytic fragment may be suitable for intramuscular administration because they are less hydrophobic than the natural molecule.

Equivalents

Those skilled in the art will recognize, or be able to ascertain using no more than routine experimentation, numerous equivalents to the specific procedures described herein. Such equivalents are considered to be within the scope of this invention and are covered by the following claims.

We claim:

1. An analogue of tissue plasminogen activator (tPA) of the formula:

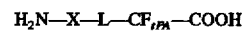

$$H_2N-X-L-CF_{tPA}-COOH$$

wherein $CF_{tPA}$ represents a catalytic fragment of tPA;

X represents a fibrin binding domain of protein A present in single or multiple units; and L represents a peptide bond linkage between X and $CF_{tPA}$ or an oligopeptide linking X and $CF_{tPA}$, wherein said analogue possesses fibrinolytic and fibrin-binding activities.

2. A tPA analogue of claim 1, wherein X is the B domain of protein A.

3. An analogue of tissue plasminogen activator (tPA) of the formula:

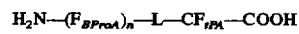

$$H_2N-(F_{BProA})_n-L-CF_{tPA}-COOH$$

Wherein $CF_{tPA}$ represents a catalytic fragment of tPA;

$F_B$ProA represents the B domain of protein A;

L represents a peptide bond or an oligopeptide linker linking $F_{BProA}$ and $CF_{tPA}$; and n is an integer from 1 to 5, wherein said analogue possesses fibrinolytic and fibrin-binding activities.

4. An analogue of claim 3, wherein $CF_{tPA}$ is the catalytic fragment spanning amino acid residues 262–527 of tPA as shown in FIG. 1 or a fragment having substantially equivalent thrombolytic activity.

5. A tPA analogue of claim 3, having the formula:

$$H_2N-F_{B\,ProA}-CF_{tpa}-COOH.$$

6. A tPA analogue of claim 3, having the formula:

$H_2N-F_{B\ ProA}-F_{B\ ProA}CF_{tPA}-COOH.$

7. An analogue of tissue plasminogen activator (tPA) comprising a domain of protein A that binds fibrin linked through its carboxy terminus to the amino terminus of a catalytic fragment of tPA, wherein said analogue possesses fibrinolytic and fibrin-binding activities.

8. An analogue of tissue plasminogen activator of claim 7, wherein the domain of protein A that binds fibrin is the B domain of protein A or multiple units thereof.

9. An analogue of tissue plasminogen activator (tPA) of the formula:

$H_2N-X_n-L-CF_{tPA}-COOH$ wherein $CF_{tPA}$ is the catalytic fragment spanning amino acid residues 262–527 of tPA as depicted in FIG. 1

X represents a fibrin binding domain of protein A;

L represents a peptide bond or an oligopeptide linker separating X and $CF_{tPA}$; and n is an integer from 1 to 5.

10. An analogue of tissue plasminogen activator (tPA), comprising a catalytic fragment of human tPA linked at its amino terminus directly to the B domain of protein A or multiple units thereof.

11. An analogue of claim 10, wherein the catalytic fragment of human tPA comprises amino acid residues 262–527 of tPA as shown in FIG. 1.

12. An analogue of tissue plasminogen activator (tPA), comprising a catalytic fragment of human tPA spanning amino acid residues 262–527 of tPA as shown in FIG. 1 linked at its amino terminus directly to a B domain of protein A.

* * * * *